United States Patent [19]

Takeda

[11] Patent Number: 5,154,085
[45] Date of Patent: Oct. 13, 1992

[54] TENSION TYPE DYNAMIC VISCOELASTICITY MEASURING APPARATUS

[75] Inventor: Haruo Takeda, Tokyo, Japan

[73] Assignee: Seiko Instruments, Inc., Tokyo, Japan

[21] Appl. No.: 748,859

[22] Filed: Aug. 23, 1991

[30] Foreign Application Priority Data

Aug. 23, 1990 [JP] Japan ............................... 2-221834

[51] Int. Cl.⁵ ............................................. G01N 3/32
[52] U.S. Cl. ........................................ 73/811; 374/47
[58] Field of Search ...................... 73/811, 808, 810; 374/47

[56] References Cited

U.S. PATENT DOCUMENTS 3,470,732 10/1969 Welhoelter et al. ................. 374/47
3,550,427 12/1970 Sueyoshi ............................ 374/47

*Primary Examiner*—Jerry W. Myracle
*Attorney, Agent, or Firm*—Spensley Horn Jubas & Lubitz

[57] ABSTRACT

A tension type dynamic viscoelasticity measuring apparatus composed of a strain detector for detecting changes in length of a specimen, an electromagnetic force generator for applying a force to the specimen, a moving mechanism for moving the electromagnetic force generator, a movement control unit for controlling the amount of movement of the moving mechanism, and a monotone function calculation unit for outputting a movement control timing to the movement control unit. The monotone function calculation unit performs a monotone function operation on the data of distance by which the moving mechanism has been moved and uses the calculation result as a movement control timing for the next movement control of the moving mechanism. As a result, this viscoelasticity measuring apparatus has a movement control loop that considers relaxation phenomena in connection with a change in length of the specimen due to stress relaxation and creep that occur in the specimen while driving the moving mechanism.

2 Claims, 1 Drawing Sheet

TENSION TYPE DYNAMIC VISCOELASTICITY MEASURING APPARATUS

BACKGROUND OF THE INVENTION

The present invention relates to tension type dynamic viscoelasticity measuring apparatus.

In conventional devices of this kind, to avoid the effects of relaxation phenomena in connection with a change in length of the specimen due to stress relaxation and creep of the specimen, a movement control timing signal is generated at a predetermined time after the previous movement control, the predetermined time being irrelevant to the distance traveled by the moving mechanism.

Since in the above-mentioned prior art devices, the next movement control is performed after a predetermined time, which is unrelated to the distance traveled by the moving mechanism, if the predetermined time is set to be a relatively short time, it offers an advantage of quicker movement control but also gives rise to the following problem: when the amount of movement of the moving mechanism is large, the next movement control timing signal occurs while the specimen is still continuing to elongate, or contract, at a high rate due to the relaxation phenomena of the specimen, making the control unstable.

Conversely, when the predetermined time interval is set to be relatively long. the above drawback is eliminated but since the number of movement controls is reduced, the measurement takes longer. A further drawback associated with a relatively long predetermined time interval arises due to the fact that when the specimen temperature has reached a transition temperature such as a glass transition temperature, the specimen elongates or contracts not only by external forces resulting from movement but also by its own property. This could be remedied by a quick control action but since the control intervals are long, there may be times when the measurement cannot be taken at the transition point, the most important section of the measuring process.

SUMMARY OF THE INVENTION

It is an object of the present invention to eliminate, or at least alleviate these problems experienced with conventional devices and procedures.

A further object of the invention is to provide a tension type viscoelasticity measuring apparatus that allows precise and quick viscoelasticity measurements.

The above and other objects are achieved, according to the present invention, by the provision of a tension type dynamic viscoelasticity measuring apparatus for measuring the viscoelasticity of a specimen which has two opposed ends, comprising:

holder means for holding one end of the specimen;

chuck means for holding the other end of the specimen;

a detection rod connected to the chuck means;

a strain detector connected to the rod for detecting changes in position of the rod;

an electromagnetic force generator connected at one end of the rod to transmit a force to the specimen through the rod and the chuck means;

a moving mechanism connected for moving the electromagnetic force generator;

dc generator means connected for causing the electromagnetic force generator to produce a dc force component;

a sinusoidal wave generator connected for causing the electromagnetic force generator to produce a time-varying sinusoidal force component;

a movement control unit connected for controlling the amount of movement of the moving mechanism; and monotone function calculation means connected to the movement control unit for receiving from the movement control unit an input signal representing the amount of movement produced by the moving mechanism during a measuring operation, the calculation means being operative for performing a monotone function operation on the input signal and for outputting a movement control timing signal to the movement control unit for controlling a time delay before performance of a next movement of the moving mechanism, the monotone function calculation means being operative for calculating a time of relaxation involved with stress relaxation and creep phenomena that occur in the specimen in proportion to the amount of movement of the moving mechanism to determine the timing of a next movement of the moving mechanism.

Preferably, the function calculation means controls the movement control unit to cause the delay preceding a movement of the moving mechanism to be linearly proportional to the magnitude of the previous movement.

When a specimen, while under a certain tension, changes in length due to thermal expansion and softening, the change in length is detected by the strain detector. At this time, the tension also changes. Hence, the moving mechanism is moved a distance L by the movement control unit according to the output of the strain detector. As the moving mechanism moves by the amount L, relaxation phenomena such as stress relaxation and creep occur in the specimen, so that the amount of strain l output from the strain detector continues to change for a relaxation time and converges to $l\infty$ regardless of the magnitude of the amount of movement L.

However, assuming an allowable variation $\Delta l$ for the strain $l\infty$, then the time it takes for the strain l to fall within the range of $l\infty \pm \Delta l$ becomes longer as the amount of movement L is larger and becomes shorter as the amount of movement L is smaller. The converging time of the strain l with respect to the amount of movement L is expressed by a monotone function for many specimens. This is a generally known fact. Based on this fact, the monotone function calculation unit takes in the amount of movement L from the movement control unit, performs the monotone function (in this case a linear function) operation on the input data and then sends the calculation result to the movement control unit as a signal indicating waiting time until the next movement control or a movement control timing signal.

The movement control unit that has received the movement control timing signal now takes in the amount of strain that is occurring at this time from the strain measuring circuit to determine the amount of movement of the moving mechanism. Since the amount of strain that is occurring while the specimen is undergoing large dimensional changes due to the relaxation phenomena is used for control purposes, the next movement control is done with precision and at an interval which is not unnecessarily large, permitting a quick and precise measurement of viscoelasticity.

In the process of measuring the dynamic viscoelasticity of specimens by utilizing tension, the object of the invention is to quickly remove changes in tension in the specimen caused by thermal expansion and softening and thereby apply an optimum tension, which is larger than alternating forces, to the specimen being measured.

Other and further objects, features and advantages of the invention will appear more fully from the following description.

BRIEF DESCRIPTION OF DRAWING

The sole FIGURE is a schematic view of one embodiment of the invention shown partly in cross section and partly in block diagram form.

DESCRIPTION OF THE PREFERRED EMBODIMENTS

Figure 1:
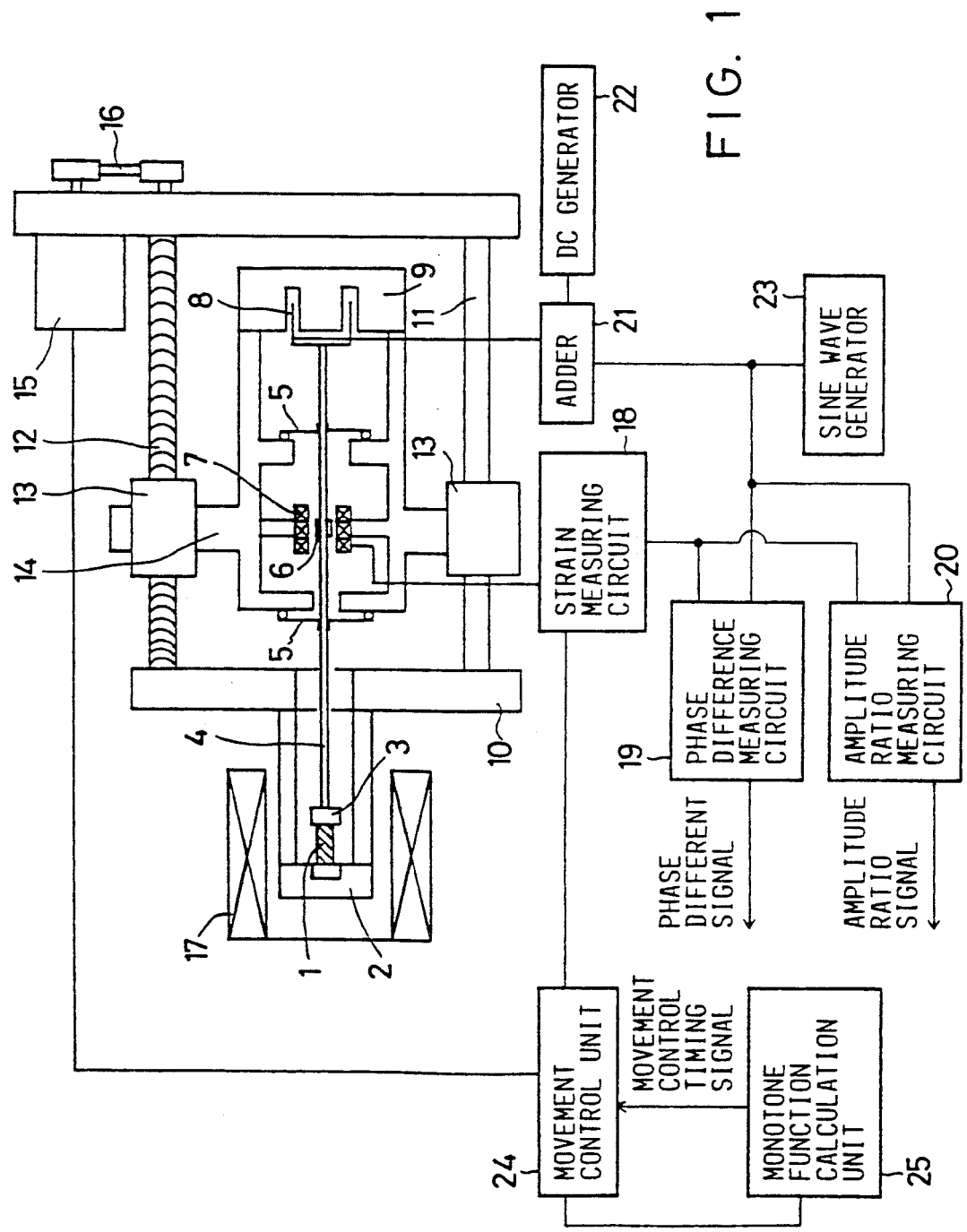

The invention will be described by referring to the sole FIGURE of the drawing that illustrates one preferred embodiment of the invention. In the FIGURE, a specimen 1 is securely clamped at one end by a specimen holder 2. The other end of specimen 1 is securely held by a specimen chuck 3 which is connected to one end of a detection rod 4. The detection rod 4 is elastically fixed to a mechanism holder 14 via two leaf springs 5 in such a way that the detection rod 4 is allowed to move in only a linear (one-dimensional) direction.

The detection rod 4 has a core 6 secured to a portion thereof, around which a differential transformer 7 is secured in the mechanism holder 14 to form a strain detector which detects displacement of core 6 relative to holder 14 as a strain of specimen 1.

Secured at the other end of detection rod 4 is a coil 8 which is surrounded by a magnet 9 secured to mechanism holder 14. Coil 8 and magnet 9 form an electromagnetic force generator.

Specimen 1 is disposed in a furnace 17 to be heated to a specified setting temperature.

A sinusoidal wave generator 23 generates a sinusoidal wave whose magnitude is adjustable, and the output of generator 23 is supplied to an adder 21 where it is added to an output voltage from a dc voltage generator 22. The output of adder 21 is applied to coil 8 which coacts with the magnet 9 to generate a force having a sinusoidal waveform with a superimposed dc component.

The force thus generated produces a strain in specimen 1 through detection rod 4 and specimen chuck 3. The strain imposed on specimen 1 is transmitted through detection rod 4 to core 6. A signal produced by differential transformer 7 is fed to a strain measuring circuit 18.

The outputs of sinusoidal wave generator 23 and strain measuring circuit 18 are supplied to a phase difference measuring circuit 19 which produces a phase difference signal.

The outputs of sinusoidal wave generator 23 and strain measuring circuit 18 are also fed to an amplitude ratio measuring circuit 20, which measures their amplitudes and produces a force (stress)-strain amplitude ratio signal.

Mechanism holder 14 is supported through bearings 13 on a ball screw 12 and a guide bar 11. As the ball screw 12 is rotated by a drive belt 16, which is driven by a stepping motor 15, the mechanism holder 14 is moved left or right. The guide bar 11, the ball screw 12, the bearings 13, the stepping motor 15 and the drive belt 16 together form a moving mechanism for the mechanism holder 14. The stepping motor 15 is operated by the output of a movement control unit 24. A monotone function calculating unit 25 determines the magnitude of the previous movement of holder 14, based on an input from movement control unit 24 as input data and derives an output signal which is a monotone, or linear, function of the input value. The monotone function calculating unit 25 sends a movement control timing signal to movement control unit 24 after a time delay which is proportional to the magnitude of the calculated result.

The movement control unit 24 also receives an input signal representing the amount of strain measured by strain measuring circuit 18.

Now, the operation of the above-described apparatus according to the invention will be described. When, with a dc-superimposed sinusoidal wave force generated by coil 8 and magnet 9 applied, the length of specimen 1 changes due to thermal expansion and softening, the strain is measured by the strain measuring circuit 18. The movement control unit 24 operates the stepping motor 15 so as to drive the moving mechanism in order to reset the strain to zero. The amount of movement is determined by movement control unit 24, based on the signal from strain measuring circuit 18, so that it is proportional to the strain detected by strain measuring circuit 18.

Movement control unit 24 then sends a signal representing the amount of movement just produced by unit 24 to monotone function calculation unit 25.

As movement control unit 24 rotates stepping motor 15 according to the amount of movement L needed to reset the strain to zero, the force produced by motor 15 is transmitted to drive belt 16, ball screw 12, bearing 13, mechanism holder 14, leaf springs 5, detection rod 4, specimen chuck 3, and specimen 1 in that order. Core 6 and coil 8 secured to detection rod 4 move together with detection rod 4.

One end of specimen 1 is fixed to specimen holder 2, which in turn is secured to a frame base 10, so that core 6 fixed to detection rod 4 moves to a point where the tension produced by the electromagnetic force of coil 8 and the restoring force of spring 5 balance each other. Then, the tension in specimen 1 continues to change during a relaxation time because of relaxation phenomena, such as stress relaxation and creep, that occur within specimen 1, so that the position of core 6 continues to change for that relaxation time.

The change in position of core 6 is measured through differential transformer 7 by strain measuring circuit 18, which outputs a signal representing the amount of strain l to movement control unit 24. The amount of strain l converges to $l\infty$ after the relaxation time.

Assuming that there is an allowable variation $\Delta l$ for the amount of strain $l\infty$, consideration will be given to the time within which the amount of strain will fall within the range of $l\infty \pm \Delta l$. This converging time becomes longer as the amount of movement L gets larger, while it becomes shorter when the amount of movement is smaller. It is generally known that the converging time of the strain l has a monotone functional relationship with respect to the amount of movement L for a large number of specimens. Based on this fact, the monotone function calculation unit 25 receives a signal representing the amount of movement L from movement control unit 24, performs a monotone function (in this case a linear function) operation on the input data and then sends the calculation result to the movement control unit 24 as a signal indicating the appropriate waiting time until the next movement control, or a movement control timing signal.

Movement control unit 24 that has received the movement control timing signal now takes in the amount of strain l that is occurring at this time from the strain measuring circuit 18 to determine the next amount of movement. Since the amount of strain that is occurring while the specimen is undergoing large changes due to relaxation phenomena is used, the next movement control is done with precision and after an interval which is not unnecessarily long, permitting a quick and precise measurement of viscoelasticity.

The movement control unit 24 and the monotone function calculation unit 25 may be formed either with analog circuits or digital circuits. The monotone function may be not only a linear function but may be a higher order function or by an exponential function. Further, the stepping motor 15 may be ant type of ac motor or dc motor. These and other modifications may be made without affecting the spirit of this invention.

This invention incorporates a movement control unit and a monotonic function calculation unit into a tension type dynamic viscoelasticity measuring apparatus, so that when the specimen undergoes a relaxation phenomenon such as stress relaxation and creep, it is possible to control the moving mechanism quickly and precisely and thereby perform a quick and precise measurement of viscoelasticity. This in turn permits widening the measuring range of the tension type dynamic viscoelasticity measuring apparatus.

This application relates to subject matter disclosed in Japanese Application No. 2-221834, filed on Aug. 23, 1990, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. A tension type dynamic viscoelasticity measuring apparatus for measuring the viscoelasticity of a specimen which has two opposed ends, comprising:

holder means for holding one end of the specimen;

chuck means for holding the other end of the specimen;

a detection rod connected to said chuck means;

a strain detector connected to said rod for detecting changes in position of said rod;

an electromagnetic force generator connected at one end of said rod to transmit a force to the specimen through said rod and said chuck means;

a moving mechanism connected for moving said electromagnetic force generator;

dc generator means connected for causing said electromagnetic force generator to produce a dc force component;

a sinusoidal wave generator connected for causing said electromagnetic force generator to produce a time-varying sinusoidal force component;

a movement control unit connected for controlling the amount of movement of said moving mechanism; and monotone function calculation means connected to said movement control unit for receiving from said movement control unit an input signal representing the amount of movement produced by said moving mechanism during a measuring operation, said calculation means being operative for performing a monotone function operation on the input signal and for outputting a movement control timing signal to said movement control unit for controlling a time delay before performance of a next movement of said moving mechanism, said monotone function calculation means being operative for calculating a time of relaxation involved with stress relaxation and creep phenomena that occur in the specimen in proportion to the amount of movement of the moving mechanism to determine the timing of a next movement of said moving mechanism.

2. Apparatus as defined in claim 1 wherein said monotone function calculation means are operative for creating a time delay which is linearly proportional to the magnitude of the immediately preceding movement produced by said moving mechanism.

* * * * *